(12) United States Patent
Breitenbach et al.

(10) Patent No.: US 6,350,398 B1
(45) Date of Patent: Feb. 26, 2002

(54) PROCESS FOR PRODUCING COATED SOLID DOSAGE FORMS

(75) Inventors: Jörg Breitenbach, Mannheim; Stephan Kothrade, Limburgerhof; Andreas Kleinke; Armin Lange, both of Heidelberg; Werner Maier, Schifferstadt, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/385,459

(22) Filed: Aug. 30, 1999

(30) Foreign Application Priority Data

Sep. 3, 1998 (DE) .......................................... 198 40 256

(51) Int. Cl.$^7$ ............................. A61K 9/32; A61K 9/36; A61K 47/32; A61K 47/34; B28B 9/06
(52) U.S. Cl. ...................... 264/129; 264/134; 264/141; 264/148; 264/151; 427/2.14; 427/2.21; 427/2.22
(58) Field of Search ................................. 264/129, 134, 264/141, 148, 151; 427/2.14, 2.21, 2.22

(56) References Cited

U.S. PATENT DOCUMENTS

| 4,801,460 | A | 1/1989 | Goertz et al. ............... 424/465 |
| 4,880,585 | A | 11/1989 | Klimesch et al. ............ 264/141 |
| 4,957,681 | A | 9/1990 | Klimesch et al. ............ 264/211 |
| 5,073,379 | A | 12/1991 | Klimesch et al. ............ 424/467 |

FOREIGN PATENT DOCUMENTS

| CA | 2209943 | 1/1998 |
| CA | 2229614 | 9/1998 |
| GB | 2249957 | 5/1992 |
| WO | 89/09066 | 10/1989 |
| WO | 96/04601 | 2/1996 |
| WO | 96/19963 | 7/1996 |
| WO | 97/15290 | 5/1997 |
| WO | 97/15291 | 5/1997 |
| WO | 97/15293 | 5/1997 |

OTHER PUBLICATIONS

*Ullmann's Enc. of Chem. Tech.*, vol. XI, 3rd ed., 1951, pp. 56–78 and 367–376.

Primary Examiner—Leo B. Tentoni
(74) Attorney, Agent, or Firm—Keil Weinkauf

(57) ABSTRACT

The invention relates to a process for producing coated solid dosage forms by forming a plastic mixture from at least one thermoplastic physiologically tolerated polymeric binder and at least one active ingredient and extruding the plastic mixture, wherein the extrudate is subsequently treated with at least one liquid or vaporized coating agent, and the coated extrudate is shaped to the required dosage form.

9 Claims, No Drawings

PROCESS FOR PRODUCING COATED SOLID DOSAGE FORMS

BACKGROUND OF THE INVENTION

1. Field of the Invention

The present invention relates to a process for producing coated solid dosage forms by forming a plastic mixture comprising at least one polymeric binder and at least one active ingredient, and extruding the plastic mixture.

Coated solid dosage forms are being used increasingly frequently, in particular for pharmaceutical purposes. Examples of coated solid dosage forms are sugar-coated tablets, film-coated tablets, dry-coated tablets, multilayer film-coated tablets and multilayer sugar-coated tablets. Sugar- and film-coated tablets are obtained by treating (coating) an active ingredient-containing binder (e.g. granules, tablet) with suitable film-forming substances intended to mask the taste of the active ingredients, increase the stability to moisture and on storage, and facilitate identification. However, the active ingredient release characteristics can also be influenced by suitable choice of the coatings. In the case of dry-coated tablets, multilayer film-coated tablets or multilayer sugar-coated tablets there is compression together of several layers of binder, as a rule in elaborate, usually multistage processes, in tableting machines. The different layers usually contain different active ingredients or active ingredients in different concentrations in order to make it possible to administer incompatible active ingredients together and/or specifically influence the release characteristics. The processes for producing such solid dosage forms are generally elaborate, multistage and therefore time-consuming and costly.

2. Description of the Related Art

A considerably simpler continuous process for producing solid drug forms has been known for some time and entails extruding a solvent-free melt of a polymeric binder containing active ingredients, and shaping this extrudate to the required drug form, for example in a calender with molding rolls, see, for example, EP-A-0 240 904 and EP-A-0 240 906. It is possible with this process to produce solid combination drug forms as described in WO 97/15293. The production of multilayer solid drug forms using this process takes place by coextrusion as described in DE 197 10 213.1, but this process is only conditionally suitable for processing the high-viscosity binders which are important for interior phases or layers for producing very slow release dosage forms because they may easily lead to blockage of the molding dies. WO 96/19963 describes a process for producing encased tablets by melt calendering, wherein the active ingredient-containing melt is introduced between two sheets of the encasing material into the calender molding rolls. However, this process is confined to thermoplastic coating compositions which can be processed as sheets.

BRIEF SUMMARY OF THE INVENTION

It is an object of the present invention to provide a continuous process for producing coated solid dosage forms which also permits the use of high-viscosity binders for interior layers and the use of a large number of coating agents.

We have found that this object is achieved by a plastic mixture being formed from at least one thermoplastic polymeric binder and at least one active ingredient and being extruded, the extrudate being treated in a second step with at least one liquid or vaporized coating agent, and subsequently the shaping being carried out.

DETAILED DESCRIPTION OF THE INVENTION

The invention therefore relates to a process for producing coated solid dosage forms by forming a plastic mixture from at least one thermoplastic physiologically tolerated polymeric binder and at least one active ingredient and extruding the plastic mixture, wherein the extrudate is subsequently treated with at least one liquid or vaporized coating agent, and the coated extrudate is shaped to the required dosage form.

To produce the plastic mixture it is necessary to mix the ingredients, namely at least one thermoplastic physiologically tolerated polymeric binder and at least one active ingredient and, where appropriate, conventional additives, and to convert them into a plastic mixture, preferably in the absence of a solvent. The plastic mixture can be formed by melting or else by kneading, mixing or homogenizing below the melting point of the binder. These process steps can be carried out in a known manner, for example as described in EP-A-0 240 904, EP-A-0 337 256, EP-A-0 358 105, WO 97/15290 and WO 97/15291. The contents of these publications are incorporated herein by reference.

The components can be first mixed and then converted into a plastic state and homogenized. However, it has proved to be preferable, especially on use of sensitive active ingredients, firstly for the polymeric binder, where appropriate together with conventional pharmaceutical additives, to be converted into the plastic state and premixed, where appropriate with alternate operation of the apparatus such as stirred vessels, agitators, solids mixers etc., and then for the sensitive active ingredient(s) to be admixed (homogenized) in "intensive mixers" in plastic phase with very short residence times. The active ingredient(s) can be employed in solid form or as solution or dispersion.

The melting and mixing take place in an apparatus customary for this purpose. Particularly suitable ones are extruders or containers which can be heated and have an agitator, e.g. kneaders (like those of the type to be mentioned below).

A particularly suitable mixing apparatus is one employed for mixing in plastics technology. Suitable apparatuses are described, for example, in "Mischen beim Herstellen und Verarbeiten von Kunststoffen", H. Pahl, VDI-Verlag, 1986. Particularly suitable mixing apparatuses are extruders and dynamic and static mixers, and stirred vessels, single-shaft stirrers with stripper mechanisms, especially paste mixers, multishaft stirrers, especially PDSM mixers, solids mixers and, preferably, mixer/kneader reactors (e.g. ORP, CRP, AP, DTB supplied by List or Reactotherm supplied by Krauss-Maffei or Ko-kneader supplied by Buss), trough mixers and internal mixers or rotor/stator systems (e.g. Dispax supplied by IKA).

In the case of sensitive active ingredients it is preferable first for the polymeric binder to be converted into the plastic state in an extruder and then for the active ingredient to be admixed in a mixer/kneader reactor. On the other hand, with less sensitive active ingredients, a rotor/stator system can be employed for vigorously dispersing the active ingredient.

The mixing apparatus is charged continuously or batchwise, depending on its design, in a conventional way. Powdered components can be introduced in a free feed, e.g. via a weight feeder. Plastic compositions can be fed in directly from an extruder or via a gear pump, which is particularly advantageous if the viscosities and pressures are high. Liquid media can be metered in by a suitable pump unit.

The mixture obtained by mixing and converting the binder, where appropriate the active ingredient and where appropriate the additive or additives into the plastic state ranges from pasty to viscous (plastic) and is therefore also extrudable. The binder should preferably be soluble or swellable in a physiological environment. Examples of suitable binders are:

Polyvinyllactams, in particular polyvinylpyrrolidone (PVP), copolymers of vinyllactams such as N-vinylpyrrolidone, N-vinylpiperidone and N-vinyl-ε-caprolactam, but in particular N-vinylpyrrolidone, with (meth)acrylic acid, (meth)acrylic esters, vinyl esters, especially vinyl acetate, copolymers of vinyl acetate and crotonic acid, partly hydrolyzed polyvinyl acetate, polyvinyl alcohol, poly(hydroxyalkyl acrylates), poly(hydroxyalkyl methacrylates), polyacrylates and polymethacrylates, copolymers of dimethylaminoethyl acrylates and methacrylic esters (e.g. Eudragit types), polyalkylene glycols, such as polypropylene glycols and polyethylene glycols (e.g. polyethylene glycol 6000), copolymers of methyl methacrylate and acrylic acid, cellulose esters, cellulose ethers, especially methylcellulose and ethylcellulose, hydroxyalkylcelluloses, especially hydroxypropylcellulose or hydroxypropylmethylcellulose, hydroxyalkylalkylcelluloses, in particular hydroxypropylethylcellulose, cellulose phthalates, especially cellulose acetate phthalate and hydroxypropylmethylcellulose phthalate, and mannans, especially galactomannans.

It is also possible to use gelatin and biodegradable polymers such as polyhydroxyalkanoates, e.g. polyhydroxybutyric acid, polylactic acid, polyamino acids, e.g. polylysine, polyasparagine, polydioxanes and polypeptides.

Preferred polymeric binders are polyvinylpyrrolidone, copolymers of N-vinyllactams, especially n-vinylpyrrolidone, and vinyl esters, copolymers of N-vinyllactams, in particular n-vinylpyrrolidone, with (meth)acrylic esters, poly(hydroxyalkyl acrylates), poly(hydroxyalkyl methacrylates), polyacrylates, polymethacrylates, alkylcelluloses and hydroxyalkylcelluloses.

One advantage of the process according to the invention is that it is suitable for binders which differ greatly in viscosity, for example for binders with K values (method of H. Fikentscher, Cellulose-Chemie 13 (1932), pp. 58–64 and 71–74) between 10 and 100, in particular between 20 and 100. The advantages of this process are particularly evident with binders having a K value>45 and preferably>50.

It must be possible to convert the polymeric binder into a plastic state in the complete mixture of all the components in the range from 50 to 180° C., preferably 60 to 130° C. The glass transition temperature of the mixture must therefore be below 200° C., preferably below 150° C. If necessary, it is reduced by conventional pharmacologically acceptable plasticizing auxiliaries. The amount of plasticizer should not exceed 30% of the total weight of binder and plasticizer in order to form storage-stable drug forms which show no cold flow. However, the mixture preferably contains no plasticizer.

Examples of such plasticizers are:

long-chain alcohols, ethylene glycol, propylene glycol, glycerol, trimethylolpropane, triethylene glycol, butanediols, pentanols such as pentaerythritol, hexanols, polyethylene glycols, polypropylene glycols, polyethylene/propylene glycols, silicones, aromatic carboxylic esters (e.g. dialkyl phthalates, trimellitic esters, benzoic esters, terephthalic esters) or aliphatic dicarboxylic esters (e.g. dialkyl adipates, sebacic esters, azelaic esters, citric and tartaric esters), fatty acid esters such as glycerol mono-, di- or triacetate or sodium diethyl sulfosuccinate. The plasticizer concentration is generally from 0.5 to 15, preferably 0.5 to 5% of the total weight of the mixture.

Conventional pharmaceutical auxiliaries, whose total amount can be up to 100% of the weight of the polymer, are, for example, extenders and bulking agents such as silicates or diatomaceous earth, magnesium oxide, aluminum oxide, titanium oxide, methylcellulose, sodium carboxymethylcellulose, talc, sucrose, lactose, cereal or corn starch, potato flour, polyvinyl alcohol, in particular in a concentration of from 0.02 to 50, preferably 0.20 to 20% of the total weight of the mixture;

lubricants and release agents such as magnesium, aluminum and calcium stearates, talc and silicones, and animal or vegetable fats, especially in hydrogenated form and those which are solid at room temperature. These fats preferably have a melting point of 50° C. or above. Triglycerides of $C_{12}$, $C_{14}$, $C_{16}$ and $C_{18}$ fatty acids are preferred. It is also possible to use waxes such as carnauba wax. These fats and waxes may be admixed advantageously alone or together with mono- and/or diglycerides or phosphatides, in particular lecithin. The mono- and diglycerides are preferably derived from the abovementioned fatty acid types. The total amount of lubricants and release agents is preferably from 0.1 to 5% of the total weight of the composition for the particular layer;

flowability agents, e.g. Aerosil, in an amount of from 0.1 to 5% of the total weight of the mixture;

dyes such as azo dyes, organic or inorganic pigments or dyes of natural origin, with preference for inorganic pigments in a concentration of from 0.001 to 10, preferably 0.5 to 3% of the total weight of the mixture;

stabilizers such as antioxidants, light stabilizers, hydroperoxide destroyers, radical scavengers, stabilizers against microbial attack.

It is also possible to add wetting agents, preservatives, disintegrants, adsorbents, mold release agents and blowing agents (cf., for example, B. H. Sucker et al. Pharmazeutische Technologie, Thieme-Verlag, Stuttgart 1978).

Auxiliaries include for the purpose of the invention substances for producing a solid solution with the pharmaceutical active ingredient. Examples of these auxiliaries are pentaerythritol and pentaerythritol tetraacetate, polymers such as polyethylene oxides and polypropylene oxides and their block copolymers (poloxamers), phosphatides such as lecithin, homo- and copolymers of vinylpyrrolidone, surfactants such as polyoxyethylene 40 stearate, and citric and succinic acids, bile acids, sterols and others as indicated, for example, by J. L. Ford, Pharm. Acta Helv. 61, 69–88 (1986).

Pharmaceutical auxiliaries are also regarded as being bases and acids added to control the solubility of an active ingredient (see, for example, K. Thoma et al., Pharm. Ind. 51, 98–101 (1989)).

The only precondition for the suitability of auxiliaries is adequate thermal stability.

Pharmaceutical active ingredients mean for the purpose of the invention all substances with a pharmaceutical effect and minimal side effects as long as they show negligible decomposition under the processing conditions. The amount of active ingredient per dose unit and the concentration can vary within wide limits depending on the activity and release rate. The only condition is that they suffice to achieve the desired effect. Thus, the concentration of active ingredient can be in the range from 0.001 to 95, preferably from 20 to 80, in particular 30 to 70% by weight. It is also possible to employ combinations of active ingredient. Active ingredients for the purpose of the invention are also vitamins and minerals, and crop treatment agents and insecticides. The vitamins include the A group, the B group, by which are meant besides $B_1$, $B_2$, $B_6$ and $B_{12}$ and nicotinic acid and nicotinamide also compounds with vitamin B properties such as adenine, choline, pantothenic acid, biotin, adenylic acid, folic acid, orotic acid, pangamic acid, carnitine, p-aminobenzoic acid, myo-inositol and lipoic acid, and vitamin C, vitamins of the D group, E group, F group, H group, I and J groups, K group and P group. Active ingredients for the purpose of the invention also include therapeutic peptides and vaccines.

The process according to the invention is suitable, for example, for processing the following active ingredients and the pharmacologically active salts thereof:
acebutolol, acetylcysteine, acetylsalicylic acid, acyclovir, alprazolam, alfacalcidol, allantoin, allopurinol, ambroxol, amikacin, amiloride, aminoacetic acid, amiodarone, amitriptyline, amlodipine, amoxicillin, ampicillin, ascorbic acid, aspartame, astemizole, atenolol, beclomethasone, benserazide, benzalkonium hydrochloride, benzocaine, benzoic acid, betamethasone, bezafibrate, biotin, biperiden, bisoprolol, bromazepam, bromhexine, bromocriptine, budesonide, bufexamac, buflomedil, buspirone, caffeine, camphor, captopril, carbamazepine, carbidopa, carboplatin, cefachlor, cefalexin, cefadroxil, cefazolin, cefixime, cefotaxime, ceftazidime, ceftriaxone, cefuroxime, selegiline, chloramphenicol, chlorhexidine, chlorpheniramine, chlortalidone, choline, cyclosporin, cilastatin, cimetidine, ciprofloxacin, cisapride, cisplatin, clarithromycin, clavulanic acid, clomipramine, clonazepam, clonidine, clotrimazole, codeine, cholestyramine, cromoglycinic acid, cyanocobalamin, cyproterone, desogestrel, dexamethasone, dexpanthenol, dextromethorphan, dextropropoxiphene, diazepam, diclofenac, digoxin, dihydrocodeine, dihydroergotamine, dihydroergotoxin, diltiazem, diphenhydramine, dipyridamole, dipyrone, disopyramide, domperidone, dopamine, doxycycline, enalapril, ephedrine, epinephrine, ergocalciferol, ergotamine, erythromycin, estradiol, ethinylestradiol, etoposide, Eucalyptus globulus, famotidine, felodipine, fenofibrate, fenoterol, fentanyl, flavin mononucleotide, fluconazole, flunarizine, fluorouracil, fluoxetine, flurbiprofen, furosemide, gallopamil, gemfibrozil, gentamicin, Gingko biloba, glibenclamide, glipizide, clozapine, Glycyrrhiza glabra, griseofulvin, guaifenesin, haloperidol, heparin, hyaluronic acid, hydrochlorothiazide, hydrocodone, hydrocortisone, hydromorphone, ipratropium hydroxide, ibuprofen, imipenem, indomethacin, iohexol, iopamidol, isosorbide dinitrate, isosorbide mononitrate, isotretinoin, itraconazole, ketotifen, ketoconazole, ketoprofen, ketorolac, labetalol, lactulose, lecithin, levocarnitine, levodopa, levoglutamide, levonorgestrel, levothyroxine, lidocaine, lipase, imipramine, lisinopril, loperamide, lorazepam, lovastatin, medroxyprogesterone, menthol, methotrexate, methyldopa, methylprednisolone, metoclopramide, metoprolol, miconazole, midazolam, minocycline, minoxidil, misoprostol, morphine, multivitamin mixtures or combinations and mineral salts, N-methylephedrine, naftidrofuryl, naproxen, neomycin, nicardipine, nicergoline, nicotinamide, nicotine, nicotinic acid, nifedipine, nimodipine, nitrazepam, nitrendipine, nizatidine, norethisterone, norfloxacin, norgestrel, nortriptyline, nystatin, ofloxacin, omeprazole, ondansetron, pancreatin, panthenol, pantothenic acid, paracetamol, penicillin G, penicillin V, phenobarbital, pentoxifylline, phenoxymethylpenicillin, phenylephrine, phenylpropanolamine, phenytoin, piroxicam, polymyxin B, povidone-iodine, pravastatin, prazepam, prazosin, prednisolone, prednisone, bromocriptine, propafenone, propranolol, proxyphylline, pseudoephedrine, pyridoxine, quinidine, ramipril, ranitidine, reserpine, retinol, riboflavin, rifampicin, rutoside, saccharin, salbutamol, salcatonin, salicylic acid, simvastatin, somatropin, sotalol, spironolactone, sucralfate, sulbactam, sulfamethoxazole, sulfasalazine, sulpiride, tamoxifen, tegafur, teprenone, terazosin, terbutaline, terfenadine, tetracycline, theophylline, thiamine, ticlopidine, timolol, tranexamic acid, tretinoin, triamcinolone acetonide, triamterene, trimethoprim, troxerutin, uracil, valproinic acid, vancomycin, verapamil, vitamin E, folinic acid, zidovudine.

Preferred active ingredients are ibuprofen (as racemate, enantiomer or enriched enantiomer), ketoprofen, flurbiprofen, acetylsalicylic acid, verapamil, paracetamol, nifedipine, captopril, omeprazole, ranitidine, tramadole, cyclosporin, trandolapril and therapeutic peptides.

It is possible specifically for solid solutions to be formed. The term "solid solutions" is familiar to the skilled worker, for example from the literature cited at the outset. In solid solutions of pharmaceutical active ingredients in polymers, the active ingredient is in the form of a molecular dispersion in the polymer.

The process according to the invention is suitable on the one hand for producing coated dosage forms which have only one coating or casing, which is usually free of active ingredient, for example sugar-coated or film-coated tablets. On the other hand, the process according to the invention makes a wide range of variation possible in the production of multilayer solid dosage forms by treating the previously formed extrudate one or more times with active ingredient-containing and/or active ingredient-free coating compositions, which makes it possible to set virtually any desired active ingredient combinations and release characteristics.

On extrusion of the plastic mixture it is advantageous to choose the temperature, viscosity and extrusion rate so as to obtain a coherent, self-supporting extrudate. This generally results in continuous production of an extrudate preferably with a constant cross section. It is also possible and advantageous, depending on the number and compatibility of the active ingredients to be employed, for multilayer extrudates, e.g. coextrudates as described in WO 96/19963, to be employed in the process according to the invention and be treated once or, where appropriate, also several times with at least one coating agent, it being possible for the binder(s) where appropriate to contain one or more active ingredients.

Extrudates are generally obtained in the form of a ribbon or a strand, preferably with a circular, oval or rounded cross section. It is also possible in specific embodiments of the process according to the invention to treat two or more extrudates, for example parallel strands or ribbons or, in particular, in the case of coextrudates, double or multiple strands together with one or more coating agents.

It is advantageous with the process according to the invention that the distance between emergence of the extrudate and application of the coating can be varied within wide limits. It is possible by altering this distance, where appropriate with the assistance of heating or cooling devices, to adjust the temperature and viscosity of the extrudate to be optimal for the subsequent coating with the coating agent. Treatment with the coating agent is generally carried out when the surface of the extrudate has cooled by at least 10° C., preferably by at least 15° C., from the temperature on emergence from the extruder die. This makes it possible also to produce multilayer dosage forms with very different properties of binder and coating agent, for example multilayer dosage forms from high viscosity binders or dosage forms with inner and outer layers which differ very greatly in melting or viscosity characteristics.

To produce multilayer or multiply coated solid dosage forms, the first treatment with a coating agent is followed by application of one or more other coating agents, which may be identical or different. Treatment with several coating agents preferably takes place successively, and the distance between the treatments is generally chosen so that the previously applied binder(s) has (have) solidified, dried or hardened, at least in part. In specific embodiments of the process according to the invention, the extrudate is treated several times with identical or different coating agents, with at least one of the coating agents containing one or more active ingredients.

Coating agents used according to the invention are preferably liquid coating agents such as melts, solutions, dispersions, emulsions or suspensions. However, vaporized coating agents are also suitable and are obtainable by vaporizing liquids and sublimable solids.

Examples of film-forming ingredients suitable for said liquid coating agents are the polymers mentioned above for the polymeric binders, in particular polyvinylpyrrolidone (PVP), copolymers of N-vinylpyrrolidone and vinyl esters such as vinyl acetate.

Likewise suitable as film-forming ingredients are gelatin, polyvinyl alcohol, alkylcelluloses such as methylcelluloses or ethylcelluloses, hydroxyalkylcelluloses such as hydroxyethyl-, hydroxypropylcellulose or hydroxypropylmethylcellulose, polyvinylpyrrolidone, certain acrylic resins such as copolymers based on dimethylaminoethyl methacrylates and methacrylic esters (Eudragit E), polyvinyl esters such as polyvinyl acetate, polyalkylene glycols such as polypropylene glycols and polyethylene glycols (e.g. polyethylene glycol 6000), certain acrylic resins such as copolymers based on methacrylic acid and methacrylic acid esters (Eudragit L and S), cellulose phthalates such as cellulose acetate phthalate or hydroxypropylmethylcellulose phthalate and mixtures thereof.

The coating agents may additionally contain auxiliaries such as plasticizers, pharmaceutical auxiliaries, lubricants and release agents, flowability agents and, where appropriate, dyes and/or active ingredients. Examples of suitable substances have already been mentioned in connection with the polymeric binders.

The film-forming ingredients can be present in the coating composition, in particular on treatment of the extrudate with the coating composition, in molten, dissolved, dispersed, suspended or vaporized form.

The coating agents may contain water or water-miscible solvents, e.g. ethanol, isopropanol, acetone or mixtures thereof. The amount of solvent is generally in the range from 2 to 30% of the total weight of coating agent.

The extrudate is generally treated with the coating agent (s) continuously, preferably by dipping, pouring, spraying, brushing or extrusion coating.

Suitable equipment for applying coating agents are well known to the skilled worker, for example from paint technology and from plastic processing (Ullmanns Enzyklopadie der chemischen Technik, Volume XI, 3rd Edition, 1951, pages 367–376, pages 42–51, pages 56–77).

The process according to the invention is suitable and advantageous for producing coatings of very diverse thicknesses. It is possible, depending on the chosen shape of the extrudate, the nature of the coating agent and the manner of treating the extrudate with the coating agent to apply total layer thicknesses between 5 $\mu$m and 750 $\mu$m, preferably between 10 $\mu$m and 500 $\mu$m. Coating agents which are free of active ingredient or have a low active ingredient content (<15% active ingredient based on the total weight of coating agent) are preferably applied in a total layer thickness of from 5 $\mu$m to 250 $\mu$m and particularly preferably from 10 $\mu$m to 150 $\mu$m. Total layer thicknesses particularly suitable for coating agents with a larger active ingredient content (active ingredient content>15% based on the total weight of coating agent) are from 150 $\mu$m to 750 $\mu$m, preferably 250 $\mu$m to 500 $\mu$m.

Said total layer thicknesses can be applied by treatment one or more times with the coating agent(s).

To achieve particular layer thicknesses or shapes of the coating it may be advantageous to pass the extrudate which has been coated with the coating agent, before hardening or complete hardening of the coating agent, through a sizer, stripper device, cylindrical knife, calibrated die or the like.

In a specific embodiment of the process according to the invention, the extrudate is treated by guiding or pulling it through a die, with the coating agent being fed in through an annular space around the die, and it being possible to adjust the coating thickness where appropriate by subsequently stripping off the excess in another die or sizer. It is moreover possible for the coating agent to be fed in both in or opposite to the direction of coating in so-called axial extrusion dies and at an angle or perpendicular to the direction of coating in so-called angled or crosshead extrusion dies. Suitable extrusion dies may also make multiple coating in one step possible.

The treatment(s) is (are) followed by the shaping to the required solid dosage form. It is possible in this to generate a large number of shapes, depending on the nature of the shaping. The form can be separated, for example, by a hot cut, i.e. by cutting or chopping the extrudate immediately after emergence from the die, or by a cold cut, i.e. by cutting or chopping the extrudate after at least partial cooling. This can be followed by further shaping steps. Thus, the dosage forms obtained by a cold cut or, in particular, by a hot cut can be rounded off to the required shape by means of rounding devices, as described in DE-A 196 29 753.

The shaping and/or separation to give the required dosage form can advantageously take place for example also by processing the coated extrudate by means of a pinch-off device as described in WO 96/04601. It is also possible, where appropriate, for the solid dosage forms which have been shaped by means of a pinch-off device to be rounded off in a second step.

The shaping and/or separation to give the required dosage form can also advantageously take place for example by processing the coated extrudate by means of a calender with molding rolls as described in EP-A 240 904, EP-A 240 906, EP-A 358 105 and WO 96/19962. The shape of the depressions and thus of the shaped dosage forms can be chosen substantially and as desired.

It is possible with said processes advantageously to produce a large number of shaped solid dosage forms, e.g. pellets, circular tablets, oblong tablets, divisible tablets, lenticular tablets, sugar-coated tablets and suppositories.

We claim:

1. A process for producing coated solid dosage forms by forming a plastic mixture comprising at least one thermoplastic physiologically tolerated polymeric binder and at least one active ingredient and extruding the plastic mixture, wherein the extrudate is subsequently treated with at least one liquid or vaporized coating agent, and the coated extrudate is shaped to the required dosage form wherein an excess of a liquid coating agent is applied to the extrudate, and the extrudate treated with the coating agent is passed through a calibrated die to strip off the excess of coating agent and thus to adjust the coating thickness and the coating shape, and the coated extrudate is shaped to the required dosage form.

2. A process as claimed in claim 1, wherein the coating of the extrudate with the coating agent takes place by dipping into or spraying with the coating agent.

3. A process as claimed in claim 1, wherein the coating agent is employed as melt, solution, dispersion, emulsion, suspension.

4. A process as claimed in claim 1, wherein a multilayer dosage form is shaped from the coated extrudate by a hot cut, cold cut, rounding off, pinching off or calendering using molding rolls.

5. A process as claimed in claim 1, wherein at least one of the coating agents employed comprises one or more active ingredients.

6. A process as claimed in claim 1, wherein the coating agent comprises as film-forming ingredient a cellulose derivative and/or a polyvinyl ester.

7. A process as claimed in claim 1, wherein the thermoplastic binder is selected from the group consisting of homo- and copolymers of N-vinyllactams, vinyl esters of saturated carboxylic acids, (meth)acrylic acids and (meth)acrylic esters.

8. A process as claimed in claim 1, wherein the thermoplastic binder has a Fikentscher K value>45.

9. A process as claimed in claim 1, wherein the extrudate to be coated is a two-layer or multilayer coextrudate.

* * * * *